United States Patent [19]

Honda et al.

[11] Patent Number: 5,138,086
[45] Date of Patent: Aug. 11, 1992

[54] METHOD FOR PREPARING α,β-UNSATURATED NITRILES

[75] Inventors: Tadatoshi Honda, Kanagawa; Sinji Tokunoh, Chiba, both of Japan

[73] Assignee: Mitsui Toatsu Chemicals, Inc., Tokyo, Japan

[21] Appl. No.: 616,934

[22] Filed: Nov. 21, 1990

[30] Foreign Application Priority Data

Nov. 30, 1989 [JP] Japan .................................. 1-309096

[51] Int. Cl.$^5$ ............................................. C07C 253/20
[52] U.S. Cl. ..................................... 558/311; 558/312; 558/313; 558/382
[58] Field of Search ................ 558/311, 312, 313, 382

[56] References Cited

U.S. PATENT DOCUMENTS

| | | | |
|---|---|---|---|
| 2,364,422 | 12/1944 | Brooks | 558/328 X |
| 2,417,748 | 3/1947 | Hagemeyer, Jr. | 558/382 |
| 2,417,749 | 3/1947 | Hagemeyer, Jr. | 558/382 |
| 2,500,403 | 3/1950 | Davis et al. | 558/382 |
| 2,723,282 | 11/1955 | Chase et al. | 558/382 |
| 2,729,670 | 1/1956 | DeBruin | 558/382 |
| 2,790,822 | 4/1957 | Wolfram et al. | 558/382 |
| 2,859,240 | 11/1958 | Holmen | 260/486 |
| 3,022,332 | 2/1962 | Sennewald et al. | 558/382 |
| 3,079,420 | 2/1963 | Sennewald et al. | 558/382 |
| 3,479,389 | 11/1969 | Eisenhauer et al. | 558/382 |

FOREIGN PATENT DOCUMENTS 1033656 7/1958 Fed. Rep. of Germany .
1069614 11/1959 Fed. Rep. of Germany .
2086892 5/1982 United Kingdom .

Primary Examiner—Joseph Paul Brust
Attorney, Agent, or Firm—Burns, Doane, Swecker & Mathis

[57] ABSTRACT

A method for preparing an α,β-unsaturated nitrile comprises bringing an α-oxycarboxylic acid amide represented by the following general formula:

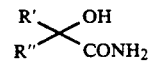

wherein R' and R" each represents a hydrogen atom or an alkyl group, with the proviso that at least one of R' and R" represents an alkyl group, into contact with a solid acid catalyst with heating in the presence of water in a molar ratio of not more than 15 with respect to the α-oxycarboxylic acid amide. The method makes it possible to directly produce an α,β-unsaturated nitrile at high yield and high selectivity utilizing an α-oxycarboxylic acid amide as a starting material, which can easily be obtained from an α-oxynitrile.

11 Claims, No Drawings

METHOD FOR PREPARING α,β-UNSATURATED NITRILES

BACKGROUND OF THE INVENTION

1. Field of the Invention

The present invention relates to a method for preparing an α, β-unsaturated nitrite in which α-oxycarboxylic acid amide is used as a starting material.

2. Description of the Prior Art

There have been known several methods for preparing α, β-unsaturated nitriles. One of such methods comprises subjecting an α-oxynitrile to a dehydration reaction, the α-oxynitrile being able to be easily and industrially synthesized from an aldehyde or a ketone and HCN in high yield. For instance, there has been known a method for preparing acrylonitrile which comprises dehydrating lactonitrile synthesized from acetaldehyde and HCN in the presence of phosphoric acid.

However, in this method, the reaction temperature is very high in the order of 600° to 700° C. and the lactonitrile as the starting material has very low thermal stability. Therefore, it is needed to rapidly raise the reaction temperature to a desired level. For this reason, it is necessary to adopt a special method in which the starting material containing phosphoric acid is sprayed into a reactor filled with a superheated gas having a temperature of 1,000° C. or higher. The selectivity of acrylonitrile in such a method is about 70% even if the method is designed as described above.

Recently, it has been found that α-oxynitrile can easily be converted into α-oxycarboxylic acid amide in high yield by subjecting it to hydration in the presence of a manganese dioxide catalyst (see U.S. Pat. No. 3,366,639).

There has not yet been proposed any method for directly preparing α, β-unsaturated nitriles from α-oxycarboxylic acid amides thus obtained at one stage, but as an indirect multistage method; U.S. Pat. No. 2,183,357 discloses a method which comprises acylating the hydroxyl and amino groups of an α-oxycarboxylic acid amide and then subjecting the acylated product to thermal decomposition. The α, β-unsaturated nitrite is one of the plurality of products formed in such a method, but the formation thereof requires the use of a high temperature; of the order of 500° C. or higher. In addition, U.S. Pat. No. 2,859,240 discloses a method for preparing an α, β-unsaturated nitrite in which an ammonium α-oxycarboxylate obtained by further hydrating the corresponding α-oxycarboxylic acid amide is used as a starting material. It is confirmed that an unsaturated nitrite is present in a distillate of the product of this method, but the formation thereof likewise requires the use of a high reaction temperature in the order of 454° to 510° C.

Moreover, U.S. Pat. No. 4,161,609 discloses a method for synthesizing an α, β-unsaturated nitrite in which an α, β-unsaturated amide is used as a starting material. However, since the method is performed with the coexistence of alcohols, the main products of the method are α, β-unsaturated esters and the yield of the α, β-unsaturated nitrite in the method is correspondingly very low. Thus, this method is not suitable for preparing an α, β-unsaturated nitrite.

As has been discussed above in detail, there has not yet been known any synthetic method for directly obtaining an α, β-unsaturated nitrite using an α-oxycarboxylic acid amide per se as a starting material.

Moreover, U.S. Pat. No. 4,464,539 discloses a method for preparing α, β-unsaturated esters and/or α, β-unsaturated carboxylic acids by reacting an α-oxycarboxylic amide with water and/or an aliphatic alcohol in the presence of a solid acid catalyst at temperatures of 150° C. or more. The reaction conditions set forth in the Examples using water only are such that the mole ratio of water to α-oxycarboxylic acid amide is the range of 17-20 in case of using water only and the reaction product is only an α, β-unsaturated carboxylic acid; the formation of α, β-unsaturated nitrite is not observed.

SUMMARY OF THE INVENTION

Accordingly, an object of the present invention is to provide a novel synthetic method for directly preparing an α, β-unsaturated nitrile from an α-oxycarboxylic acid amide, as a starting material, which can easily be prepared from the corresponding α-oxynitrile.

Thus, according to the present invention, there is provided a novel method for preparing an α, β-unsaturated nitrile in which an α-oxycarboxylic acid amide represented by Formula I is brought into contact with a solid acid catalyst while heating in the presence of water of not more than 15 moles per 1 mol of the α-oxycarboxylic acid amide:

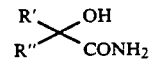

wherein R' and R" are hydrogen or a lower alkyl group, provided that at least one of R' and R" is a lower alkyl group.

DESCRIPTION OF THE PREFERRED EMBODIMENTS

α-Oxycarboxylic acid amides used as the starting materials of the present invention can easily be prepared according to the method described in U.S. Pat. No. 3,366,639 which comprises subjecting α-oxynitriles to hydration in the presence of a manganese dioxide catalyst.

The catalysts used in the method of the present invention are, for instance, those comprising a salt of phosphoric acid with at least one element selected from the group consisting of Group 1, 2, 3, 4, 5, 6, 7, 8, 9, 10, 11, 12, 13 and 14 of Periodic Table (according to the revised IUPAC nomenclature of inorganic compounds (1989)); solid phosphoric acid catalysts; those comprising a sulfate of at least one element selected from the group consisting of Li, Na, K, Rb, Cs, Be, Ca, Mg, Sr, Ba, Cr, Mn, Fe, Co, Ni, Cu, Zn, Cd, Al, In, Tl, Sn and Pb; or those comprising an oxide of at least one element selected from the group consisting of Be, Mg, Y, La, Ce, Th, U, Ti, Zr, V, Cr, Mn, Fe, Ni, Co, Cu, Zn, Cd, B, Al, Si, Sb and Bi.

Preferred catalysts comprising a phosphate among the solid acid catalysts include, for instance, those comprising a phosphate of at least one element selected from the group consisting of Groups 2, 3 and 13 of the Periodic Table and preferred catalysts comprising an oxide include, for instance, those comprising an oxide of at least one element selected from the group consisting of Group 2, 3 and 13 of the Periodic Table and the use thereof can provide excellent effects.

In the catalysts comprising a phosphoric acid salt among these catalysts, the atomic ratio (M/P) of the element (M) to the phosphorus atom (P) ranges from 0 to 3 wherein M/P =0 corresponds to the solid phosphoric acid catalyst. The structures of these phosphoric acid salts are not limited to specific ones. These phosphates may be prepared according to any known method. For example, the method disclosed in Preparative Inorganic Reactions, 1965,2 , pp. 139-167 can in general be adopted, the method comprising reacting a metal, a metal oxide or a metal salt with phosphoric acid or a phosphate. Alternatively, the phosphates can also be prepared according to a method comprising reacting a metal alcoholate with phosphoric acid.

Moreover, these phosphates, sulfates or oxides may, in general, be supported on a carrier such as active carbon, silica, silica-alumina or alumina. Such a carrier-supported catalyst can be obtained according to any known method such as a kneading or dipping method.

The catalyst used in the method of this invention may comprise two or more of these phosphates, sulfates and oxides.

$\alpha$-Oxycarboxylic acid amides used in the method of the present invention as starting materials are represented by the above Formula I. In case of R' and R'' being a lower alkyl group, the carbon atoms are preferably within the range of 1 to 3.

Such $\alpha$-oxycarboxylic acid amides include a variety of $\alpha$-oxycarboxylic acid amides and specific examples thereof are lactamide, $\alpha$-oxybutyramide, $\alpha$-oxyisobutyramide, $\alpha$-oxyvalelamide, $\alpha$-oxyisovalelamide, $\alpha$-methyl-$\alpha$-oxybutyramide.

In the method of the present invention, the reaction is performed by bringing the reactant into contact with the solid acid catalyst, but the reaction mixture may be gaseous, liquid or qas-liquid mixed phase. In general, gaseous phase or gas-liquid mixed phase is suitably employed. The contact between them can be performed by any manner such as a fixed bed system, a fluidized bed system or a moving bed system.

The reaction temperature, in general, ranges from 250° to 450° C., preferably 280° to 450° C. and more preferably 300° to 400° C. This is because, if the temperature is less than 250° C., the reaction rate is low and is not practically applicable, while if it is more than 450° C., the $\alpha$-oxycarboxylic acid amide as the starting material is severely decomposed.

The contact time between the reactant and the catalyst may widely vary depending on the kind of the catalysts used and the reaction conditions such as the reaction temperature, but, in general, ranges from 0.5 to 360 seconds.

The reaction may be carried out at normal pressure, under an elevated pressure or at a reduced pressure.

In addition, the reaction may be performed in the presence of an inert gas such as nitrogen gas, water vapor or carbon dioxide gas. It is also possible to perform the reaction in the coexistence of ammonia gas or acetóne vapor.

If the reaction is carried out in the presence of water vapor, the molar ratio of water to the $\alpha$-oxycarboxylic acid amide is very important and greatly affects the yield and selectivity of the corresponding $\alpha$, $\beta$-unsaturated nitrile.

If the reaction is carried out in the presence of water vapor, the water vapor is supplied to the reaction system in a molar ratio of not more than 15, preferably not more than 10 and more preferably not more than 5. Though the lower limit of water is not particularly limited, it may be 0.1 mol per mol of the $\alpha$-oxycarboxylic acid amide.

The method of the present invention does not require the presence of an alcohol and the presence thereof is rather detrimental in the method of this invention since the yield and selectivity of the desired $\alpha$, $\beta$-unsaturated nitrile are impaired as will be discussed in the following Comparative Example 1.

After the completion of the catalytic reaction and cooling the reaction product mixture, the resulting reaction solution is, in general, subjected to known subsequent treatments such as distillation, rectification and/or extraction to separate or isolate the desired $\alpha$, $\beta$-unsaturated nitrile.

The method of the present invention will hereinafter be explained in more detail with reference to the following non-limitative working Examples and the effects practically attained by the present invention will also be discussed in detail in comparison with Comparative Examples.

EXAMPLE 1

50 g of lanthanum nitrate was dissolved in 200 g of pure water. To the resulting aqueous solution, there was dropwise added a solution obtained by diluting 17 q of 85% phosphoric acid with 20 g of pure water over 20 minutes under stirring. The reaction solution was maintained at 60 for one hour for ripening and then pH thereof was adjusted to 9 with the addition of ammonia. The resulting precipitates were washed with 0.1 M aqueous solution of ammonium carbonate according to a decantation method, then filtered under reduced pressure and dried at 120° C. The resultant solid was pulverized, formed into tablets and calcined at 700° C. for 4 hours. The tableted and calcined catalyst was again pulverized to prepare pulverized catalyst of 20 mesh on.

8.6 cc of the pulverized catalyst was packed in a reaction tube of hard glass having an inner diameter of 17 mm, 10 cc of molten alumina balls having a diameter of 1 mm were put on the catalyst layer, this serving as the starting material-evaporation zone and the reaction tube was fixed in an electric furnace maintained at 350° C.

A 60 wt% aqueous solution of $\alpha$-oxyisobutyric acid amide (the molar ratio of water to $\alpha$-oxyisobutyric acid amide: 3.8) was supplied to the upper portion of the reaction tube, i.e., the starting material-evaporation zone in a flow rate of 6.3 g/hr in a nitrogen gas stream of 15 cc/min.

The gases which passed through the catalyst layer were separated into condensates and non-condensed substances through a cold trap and were analyzed by a gas chromatography method. The yield of methacrylonitrile with respect to the starting $\alpha$-oxyisobutyric acid amide was 84% and the selectivity thereof was 88%.

EXAMPLE 2

The same procedure used in Example 1 was repeated except that catalysts listed in the following Table 1 were substituted for the catalyst used in Example 1 and the following results were obtained.

TABLE 1

| Type of Catalyst | Methacrylonitrile | |
|---|---|---|
| | Yield (%) | Selectivity (%) |
| PrPO$_4$ | 85 | 91 |
| CePO$_4$ | 83 | 87 |

TABLE 1-continued

| Type of Catalyst | Methacrylonitrile | |
|---|---|---|
| | Yield (%) | Selectivity (%) |
| Sr(HPO$_4$) | 80 | 81 |
| AlPO$_4$ | 56 | 68 |
| Mg(H$_2$PO$_4$)$_2$ | 78 | 78 |
| SiO$_2$—MgO | 23 | 42 |

EXAMPLE 3

The same procedures used in Examples 1 and 2 were repeated except that the reaction temperature was changed to 280° C. and thus the results listed in the following Table 2 were observed.

TABLE 2

| Type of Catalyst | Methacrylonitrile | |
|---|---|---|
| | Yield (%) | Selectivity (%) |
| La(HPO$_4$)$_2$ | 15 | 45 |
| PrPO$_4$ | 17 | 44 |
| CePO$_4$ | 13 | 48 |
| Sr(HPO$_4$) | 14 | 46 |
| AlPO$_4$ | 10 | 40 |
| Mg(H$_2$PO$_4$)$_2$ | 13 | 45 |
| SiO$_2$—MgO | 8 | 32 |

EXAMPLE 4

The same procedures used in Examples 1 and 2 were repeated except that a 37 wt % aqueous solution of α-oxyisobutyramide as the starting material (molar ratio of water to the starting material: 9.7) was used and the results listed in the following Table 3 were observed.

TABLE 3

| Type of Catalyst | Methacrylonitrile | |
|---|---|---|
| | Yield (%) | Selectivity (%) |
| La(HPO$_4$)$_2$ | 81 | 83 |
| PrPO$_4$ | 85 | 86 |
| CePO$_4$ | 79 | 81 |
| Sr(HPO$_4$) | 75 | 76 |
| AlPO$_4$ | 53 | 60 |
| Mg(H$_2$PO$_4$)$_2$ | 75 | 75 |
| SiO$_2$—MgO | 32 | 38 |

EXAMPLE 5

The same procedures used in Examples 1 and 2 were repeated except that a 28 wt % aqueous solution of α-oxyisobutyramide as the starting material (molar ratio of water to the starting material: 14.7) was used and the results listed in the following Table 4 were observed.

TABLE 4

| Type of Catalyst | Methacrylonitrile | |
|---|---|---|
| | Yield (%) | Selectivity (%) |
| La(HPO$_4$)$_2$ | 39 | 39 |
| PrPO$_4$ | 41 | 41 |
| CePO$_4$ | 40 | 40 |
| Sr(HPO$_4$) | 37 | 37 |
| AlPO$_4$ | 27 | 29 |
| Mg(H$_2$PO$_4$)$_2$ | 38 | 39 |
| SiO$_2$—MgO | 18 | 22 |

EXAMPLE 6

The same procedure used in Example 1 was repeated except that a 60 wt % aqueous solution of lactic acid amide (molar ratio of water to lactic acid amide: 3.3) was substituted for the 60 wt % aqueous solution of α-oxyisobutyric acid amide. As a result, it was found that the yield of acrylonitrile with respect to the starting material, lactamide, was 86% and the selectivity of acrylamide was 87%.

EXAMPLE 7

The same procedure used in Example 1 was repeated except that α-oxybutyramide was substituted for the α-oxyisobutyramide used in Example 1 and as a result, β-methyl acrylonitrile was obtained in an yield of 83%.

COMPARATIVE EXAMPLE 1

The same procedures used in Examples 1 and 2 were repeated except that a 14 wt % solution of α-oxyisobutyramide in methanol was supplied at a flow rate of 27 g/hr as the starting material and the results listed in the following Table 5 were observed.

TABLE 5

| Type of Catalyst | Methacrylonitrile | |
|---|---|---|
| | Yield (%) | Selectivity (%) |
| La(HPO$_4$)$_2$ | 2 | 2 |
| PrPO$_4$ | 1 | 1 |
| CePO$_4$ | 2 | 2 |
| Sr(HPO$_4$) | 1 | 1 |
| AlPO$_4$ | 4 | 4 |
| Mg(H$_2$PO$_4$)$_2$ | 2 | 2 |
| SiO$_2$—MgO | 6 | 7 |

In any case, the principal product was methyl methacrylate.

COMPARATIVE EXAMPLE 2

The same procedure used in Example 3 was repeated except that a 22 wt % aqueous solution of α-oxyisobutyramide (molar ratio of water to α-oxyisobutyramide: 20.3) was used as the starting material and the results listed in the following Table 6 were observed. In any case, the principal product was methacrylic acid.

TABLE 6

| Type of Catalyst | Methacrylonitrile | |
|---|---|---|
| | Yield (%) | Selectivity (%) |
| La(HPO$_4$)$_2$ | 0 | 0 |
| PrPO$_4$ | 0 | 0 |
| CePO$_4$ | 0 | 0 |
| Sr(HPO$_4$) | 0 | 0 |
| AlPO$_4$ | 0 | 0 |
| Mg(H$_2$PO$_4$)$_2$ | 0 | 0 |
| SiO$_2$—MgO | 0 | 0 |

COMPARATIVE EXAMPLE 3

The same procedure of Example 3 was repeated except that the starting materials were prepared to be a mole ratio of α-oxyisobutyramide/methanol/water of 1/16/10. The results obtained are set forth in Table 7.

TABLE 7

| Type of Catalyst | Methacrylonitrile | |
|---|---|---|
| | Yield (%) | Selectivity (%) |
| La(HPO$_4$)$_2$ | 0 | 0 |
| PrPO$_4$ | 0 | 0 |
| CePO$_4$ | 0 | 0 |
| Sr(HPO$_4$) | 0 | 0 |
| AlPO$_4$ | 0 | 0 |
| Mg(H$_2$PO$_4$)$_2$ | 0 | 0 |
| SiO$_2$—MgO | 0 | 0 |

In any case, the main products were methyl methacrylate and methacrylic acid.

As has been explained above in detail, the novel method for directly synthesizing an α, β-unsaturated nitrile is provided according to the present invention.

More specifically, according to the method of the present invention, α, β-unsaturated nitriles can be obtained in high yield and high selectivity by heating an α-oxycarboxylic acid amide as a starting material, which can easily be obtained from an α-oxynitrile together with a proper amount of water or water vapor (the molar ratio of water to the starting material is not more than 15) in the presence of a solid acid catalyst.

What is claimed is:

1. A method for preparing an α, β-unsaturated nitrile comprising (i) contacting an α-oxycarboxylic acid amide represented by the following formula:

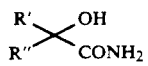 I wherein R' and R" represents a hydrogen atom or a lower alkyl group, with the proviso that at least one of the groups R' and R" represent a lower alkyl group, with a solid acid catalyst, while heating in the presence of water but said water being present in a mole ratio of water to α-oxycarboxylic acid amide of not more than 15, and (ii) obtaining a product comprising an α, β-unsaturated nitrile as the main component.

2. A method according to claim 1, wherein the solid acid catalyst is a catalyst comprising a phosphate, said phosphate being one of at least one element selected from the group consisting of the Group 1, 2, 3, 4, 5, 6, 7, 8, 9, 10, 11, 12, 13 and 14 elements of Periodic Table according to the revised IUPAC nomenclature of inorganic compounds (1989), or a solid phosphoric acid catalyst.

3. A method according to claim 1, wherein the solid acid catalyst is a catalyst comprising a phosphate, said phosphate being one of at least one element selected from the group consisting of Group 2, 3 and 13 elements of the Periodic Table.

4. A method according to claim 1, wherein the solid acid catalyst comprising a sulfate, said sulfate being one of at least one element selected from the group consisting of Li, Na, K, Rb, Cs, Be, Ca, Mg, Sr, Ba, Cr, Mn, Fe, Co, Ni, Cu, Zn, Cd, Al, In, Tl, Sn and Pb.

5. A method according to claim 1, wherein the solid acid catalyst ia a catalyst comprising an oxide, said oxide being one of at least element selected from the group consisting of Be, Mg, Y, La, Ce, Th, U, Ti, Zr, V, Cr, Mn, Fe, Ni, Co, Cu, Zn, Cd, B, Al, Si, Sb and Bi.

6. A method according to claim 1, wherein the solid acid catalyst is a catalyst comprising an oxide, said oxide being one of at least element selected from the group consisting of Group 2, 3, and 13 elements of the Period Table.

7. A method according to claim 1, wherein the contact between the catalyst and the starting material is carried out at a temperature of not less than 2502 C. but not more than 4350° C.

8. A method according to claim 1, wherein the mole ratio of water to α-oxycarboxylic acid amide is within the range of 0.1 to 15.

9. A method according to claim 8, wherein the mole ratio of water to α-oxycarboxylic acid amide is not more than 10.

10. A method according to claim 9, wherein the mole ratio is not more than 5.

11. A method according to claim 1, wherein step (i) is carried out in the absence of alcohol.

* * * * *

UNITED STATES PATENT AND TRADEMARK OFFICE
CERTIFICATE OF CORRECTION

PATENT NO. : 5,138,086
DATED : August 11, 1992
INVENTOR(S) : Honda et al.

It is certified that error appears in the above-identified patent and that said Letters Patent is hereby corrected as shown below:

In column 8, line 9, before "comprising" insert --is a catalyst--.

In column 8, line 15, before "element" insert --one--.

In column 8, line 20, before "element" insert --one--.

In column 8, line 25, amend "2502" to --250°--.

In column 8, line 26, amend "4350°" to --450°--.

Signed and Sealed this

Twenty-fifth Day of January, 1994

Attest:

BRUCE LEHMAN

*Attesting Officer*  *Commissioner of Patents and Trademarks*